United States Patent [19]

Hawman

[11] Patent Number: 5,390,225
[45] Date of Patent: Feb. 14, 1995

[54] MAPPING SLICES OF THE HUMAN BODY INTO REGIONS HAVING A CONSTANT LINEAR ATTENUATION COEFFICIENT FOR CORRECTING IMAGES ACQUIRED DURING A NUCLEAR MEDICINE STUDY FOR ATTENUATION ARTIFACTS

[75] Inventor: Eric G. Hawman, Schaumburg, Ill.

[73] Assignee: Siemens Medical Systems, Inc., Iselin, N.J.

[21] Appl. No.: 905,947

[22] Filed: Jun. 29, 1992

[51] Int. Cl.⁶ .............................................. G01T 1/166
[52] U.S. Cl. .......................................... 378/6; 378/5; 378/87; 378/901
[58] Field of Search .................. 250/363.04, 370.09; 378/4, 5, 6, 7, 8, 86, 87, 901; 364/413.13, 413.24

[56] References Cited

U.S. PATENT DOCUMENTS

| | | | |
|---|---|---|---|
| 4,633,398 | 12/1986 | Gullberg et al. | 364/413.21 |
| 5,155,365 | 10/1992 | Cann et al. | 250/363.02 |
| 5,210,421 | 5/1993 | Gullberg et al. | 250/363.04 |
| 5,289,008 | 2/1994 | Jaszczak et al. | 250/363.03 |
| 5,293,195 | 3/1994 | Berlad et al. | 364/413.24 |
| 5,315,506 | 5/1994 | Wang et al. | 364/413.19 |

FOREIGN PATENT DOCUMENTS 0145998  6/1985  European Pat. Off. .

OTHER PUBLICATIONS

Budinger et al., "Three-Dimensional Reconstruction in Nuclear Medicine Emission Imaging" IEEE Transactions on Nuclear Science, vol. NS-21, Jun. 1974, pp. 2–20.

Fleming, "A Technique for Voice CT Images in Attenuation Correction and Quantifications in SPECT" Nuclear Medicine Commucations 10, pp. 83–98, Jun. 88–89, Chapman and Hall Ltd.

J. C. Yanch, M. A. Flower & S. Webb, A Comparison of Deconvolution and Windowed Subtraction Techniques for Scatter Compensation in SPECT, Mar. 1988, pp. 13–20, IEEE Transactions on Medical Imaging, N.Y., vol. 7, No. 1.

Stephen H. Manglos et al., Nonisotropic Attenuation in SPECT: Phantom Tests of Quantitative Effects and Compensation Techniques, Oct. 1987, pp. 1584–1591, Journal of Nuclear Medicine No. 10 N.Y.

Dale L. Bailey et al., Improved SPECT Using Simultaneous Emission and Transmission Tomography, May 1987, pp. 844–851, Journal of Nuclear Medicine No. 5 N.Y.

Soo Chin Liew et al., Noise, Resolution, and Sensitivity Considerations in the Design of a Single-Slice Emission-Transmission Computed Tomographic System, Oct. 1991, pp. 1002–1015 Medical Physics (18) No. 5 N.Y.

Primary Examiner—Paul M. Dzierzynski
Assistant Examiner—David V. Bruce
Attorney, Agent, or Firm—Mark H. Jay

[57] ABSTRACT

An energy window of a scintillation camera system is set to include only events which have been Compton-scattered within a slice of the body of a patient undergoing a SPECT examination. From events so acquired, a scatter image is reconstructed. The scatter image is processed to define therewithin a plurality of regions of constant attenuation coefficient. This information can be used during the normal image reconstruction process to eliminate artifacts caused by variation in attenuation coefficient.

5 Claims, 5 Drawing Sheets

MAPPING SLICES OF THE HUMAN BODY INTO REGIONS HAVING A CONSTANT LINEAR ATTENUATION COEFFICIENT FOR CORRECTING IMAGES ACQUIRED DURING A NUCLEAR MEDICINE STUDY FOR ATTENUATION ARTIFACTS

BACKGROUND OF THE INVENTION

This invention relates to nuclear medicine, and more particularly relates to SPECT studies which are carried out to form tomographic images of the uptake of radioisotopes within body organs. In its most immediate sense, the invention relates to attenuation correction of data used in SPECT studies of, e.g., the heart.

In a conventional SPECT (Single Photon Emission Computed Tomography) study of an organ such as the heart, a radioisotope (Tc-99m, Tl-201, for example) is administered to the patient and the radioisotope is taken up by the heart muscles. Then, the patient is placed in a scintillation camera system and one or more scintillation camera detectors are rotated about the long axis of the patient. These detectors pick up gamma radiation which leaves the patient, and the resulting data is used to form three-dimensional images ("SPECT images" or "tomographic images") of the distribution of the radioisotope within the patient.

Such three dimensional SPECT images can be calculated based on a set of two-dimensional images ("projections" or "projection images") acquired by the scintillation camera system; this calculation process is known as image reconstruction. The most commonly employed method of image reconstruction is known as "filtered backprojection". When filtered backprojection reconstruction is used to reconstruct SPECT images from scintigraphic projection images obtained from a scintillation camera, some well-known distortions introduce errors ("artifacts") in the result. One of the most important distortions is caused by attenuation of gamma radiation in tissue.

As a consequence of attenuation, image values in the various projections do not represent line integrals of the radioisotope distribution within the body. It is therefore necessary to correct for this, and the process for doing so in SPECT is known as attenuation correction.

Many techniques for attenuation correction in SPECT assume that the linear attenuation coefficient of the body is uniform and impose such uniformity as a mathematical constraint in the image reconstruction process. However, for a very important class of studies, namely cardiac SPECT studies, the linear attenuation coefficient of the body is in fact highly nonuniform. This is because lung tissue has a lower attenuation than do, e.g., the blood and other non-lung tissue.

Thus, in SPECT studies of, e.g., the heart, a SPECT reconstruction of the image of radioactivity within the heart will necessarily contain artifacts caused by the unequal attenuation coefficients of, e.g., the lungs and the body (and, in the case of some female patients, large breast size.)

It would therefore be advantageous to provide a method for mapping a slice of a patient's body into regions of different attenuation coefficients, thereby permitting the reconstruction process to be carried out on the basis of the patient's actual body structure and without the need to use an overly simplistic modelling assumption, namely, that the entire body has a single attenuation coefficient.

It would further be advantageous to provide a such a method which would actually permit such different attenuation coefficients to be computed, thereby permitting the backprojection process to be carried out on the basis of the actual attenuation coefficients in the patient under study.

It would additionally be advantageous to provide such a method which would add little if any time to the duration of a conventional SPECT study, thereby not diminishing patient throughput through the camera.

In accordance with the invention, the scintillation camera system is set so that Compton-scattered events fall within an energy window, and a scatter image is formed from Compton-scattered events which are acquired during a SPECT study. Because Compton-scattering of gamma rays is the primary attenuation process in body tissue at energies of interest in nuclear medicine, the scatter image will reflect, in a general way, regions of differing attenuation coefficients. In further accordance with the invention, this scatter image is processed so as to define within it bounded regions within which the attenuation coefficient may accurately be treated as constant.

Therefore, in accordance with the invention, a slice of the patient's body is mapped into bounded regions, each region having a single attenuation coefficient. As a result, the backprojection algorithms used in the reconstruction process can take account of the spatial variation in the attenuation coefficient within the patient's body, and need not make the inaccurate assumption that the attenuation coefficient is constant within the body.

In the preferred embodiment, the SPECT event acquisition process takes place with two energy windows simultaneously, one window encompassing only Compton-scattered events and the other window encompassing photopeak events from the radioisotope used in the study. This has the consequence that the study is not prolonged since the scatter image and the conventional nuclear medicine image can be acquired and reconstructed simultaneously, just as can be a conventional dual-isotope study.

Once the scatter image has been formed, it may advantageously be processed in order to more accurately define the boundaries of the regions therewithin. After such processing, the attenuation coefficients of the regions may simply be supplied on the basis of known data, e.g. predetermined lookup tables. Alternatively, the actual attenuation coefficients may be calculated by directing gamma rays through the body and solving a system of equations. This latter procedure might be desirable where predefined tables could be seriously wrong, as in instances of pulmonary congestion.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
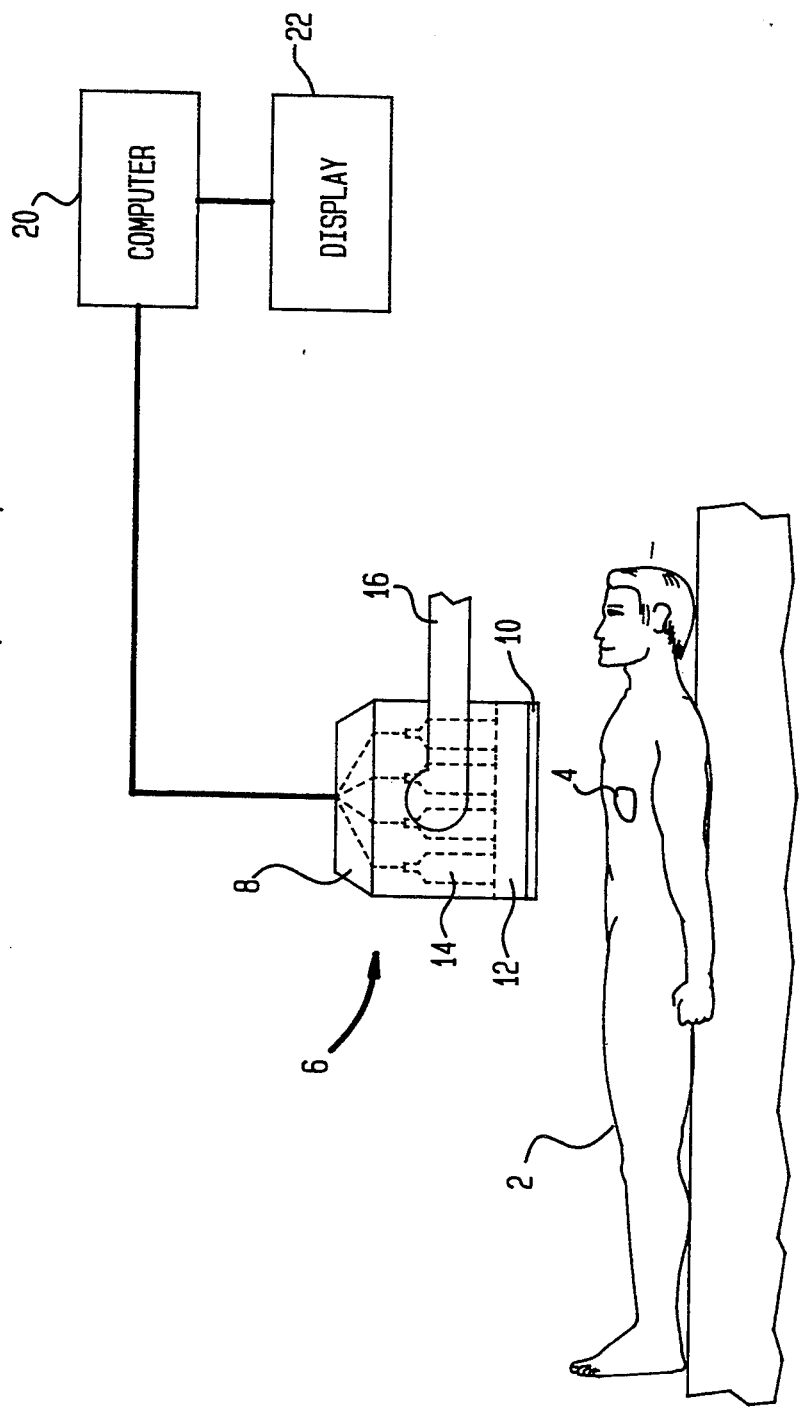
FIG. 1 is a schematic diagram of a conventional SPECT scintillation camera system.

FIG. 1 schematically shows how a cardiac SPECT study is conducted upon a patient 2. In such a study, a radioisotope is administered to the patient 2; the radioisotope is taken up by the muscles of the heart 4. Because of this uptake, gamma rays are emitted from the heart 4 in all directions. In a conventional scintillation camera system 6 with one or more detectors 8 (only one is shown, the number of detectors 8 forming no part of the present invention), the gamma rays are collimated by a lead collimator 10 and enter the detector 8, becoming incident upon a scintillation crystal 12 of, e.g. NaI(T1). The gamma radiation interacts with the scintillation crystal 12, producing minute flashes of scintillation light ("events") which are detected by an array 14 of photomultiplier tubes. This array 14 produces electrical signals, from which the brightnesses and locations of the events may be determined. As the study progresses, the detector 8 is rotated around the patient by a gantry 16; in a conventional SPECT study using scintillation camera systems manufactured by Siemens Gammasonics, Inc., assignee of the present application, the detector is rotated to 64 positions, or stations. At each such station, a planar image of the radioactivity distribution within the heart 4 is acquired. All such images are routed to a computer 20, which reconstructs the images to form a tomographic (three-dimensional) image of the distribution of the radioisotope taken up within the heart 4; this image can be displayed upon a display 22.

Figure 2:
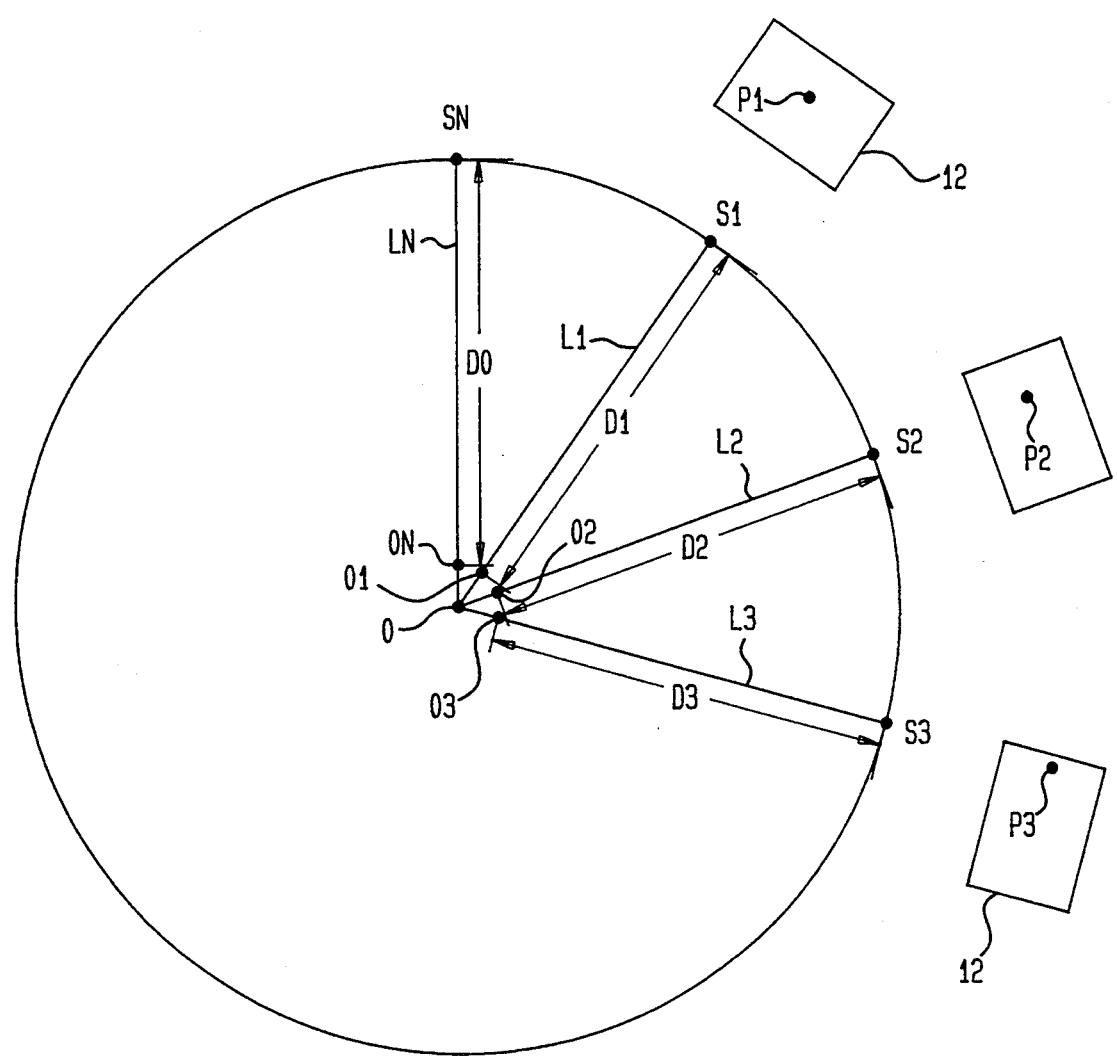
FIG. 2 shows how a nuclear medicine image is reconstructed by backprojection of a set of planar images taken at different stations around the patient.

For purposes of this application, the concept of image reconstruction has been illustrated in FIG. 2, which relates to reconstruction of a single point in the body located at the origin 0. (Filtered backprojection is not actually carried out in this way, but for purposes of this application, a description of a filtered backprojection algorithm is not necessary.) As can be seen in FIG. 2, planar images of the distribution of the radioisotope within the heart 4 are acquired at a plurality of rotational stations around the patient, there being n stations S1, S2, . . . Sn. (As stated above, in conventional SPECT scintillation camera systems as manufactured by Siemens Gammasonics, Inc., assignee of the present application, n equals 64.)

At station S1, gamma rays having an intensity I0 at the origin O will be detected as having intensity I1 and position P1. (Position P1 is the location of the detected scintillation event within the plane of the scintillation crystal and is a two-dimensional vector.) Because the gamma rays have passed through the collimator 10 (it is here assumed that the collimator 10 is of the parallel hole type, but this is only for simplicity of description), it is known that 0 must lie along line L1. Furthermore, since I1 is related to I0 by the "inverse square" law and assuming that the patient has a homogeneous attenuation coefficient, I1 is characteristic of the distance D1 between the origin O and the detector at station S1. Thus, the apparent location of the origin O is at location O1.

However, this does not by itself locate the origin O in space. To do this, it is necessary to observe the origin O from at least one additional location (advantageously, from more than one additional location.) Thus, at station S2, gamma rays emitted from the origin O will appear at position P2 and will have an intensity I2, indicating that the origin O is distant by a distance D2 from the detector along line L2. Thus, the apparent location of the origin O is at location O2 from station S2. The same holds true for each of the n stations. If the attenuation coefficient of the body is entirely homogeneous, it can reasonably be expected that all the detected locations O1, O2 . . . On will be reasonably coincident at or about 0, as is shown in FIG. 2.

It may therefore be understood that a tomographic image of radioisotope uptake within a body organ may be built up by acquiring millions of events at the various stations S1 . . . Sn and "backprojecting" them in the above manner. This procedure is known as a SPECT study.

Figure 3:
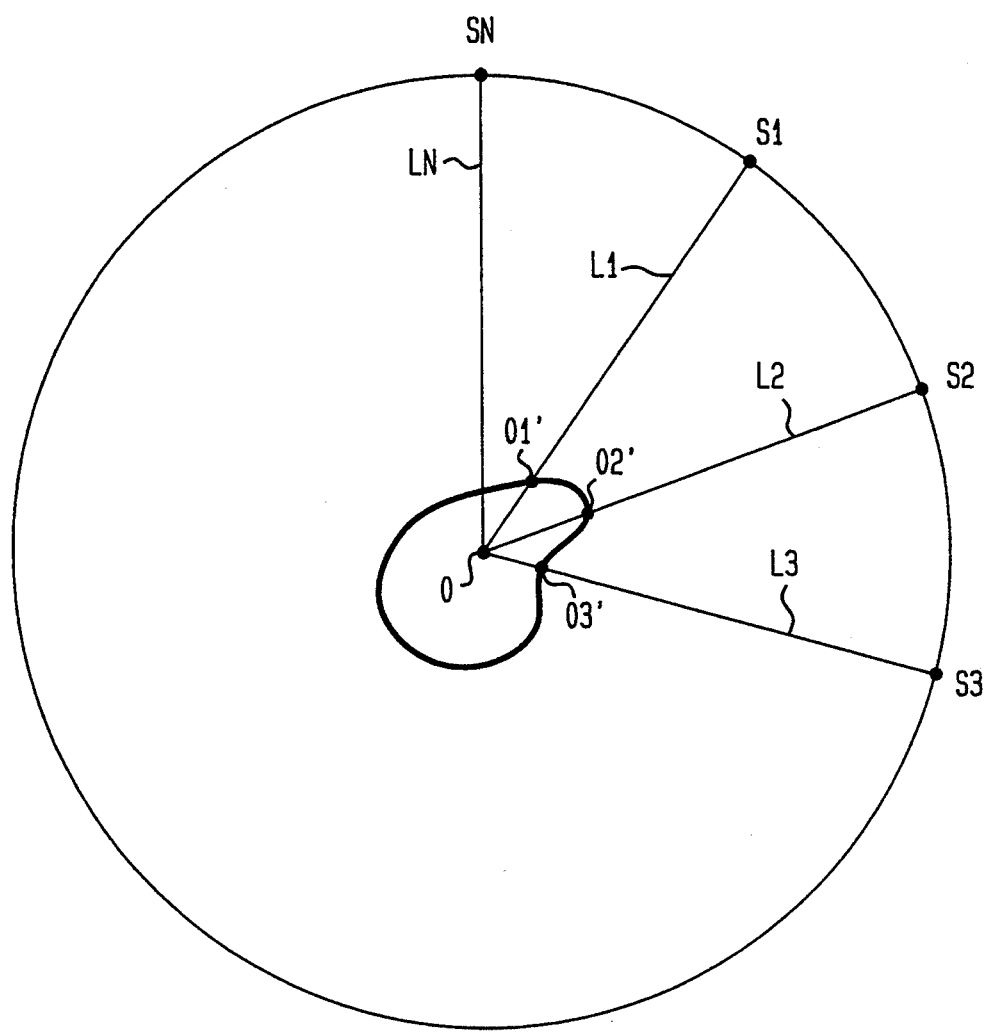
FIG. 3 shows how the FIG. 2 reconstruction process is adversely affected as a result of attenuation artifacts.

However, as is illustrated in FIG. 3, let it be assumed that the attenuation coefficient within the body of the patient varies greatly from each station to the next. In this instance, the detected locations O1', O2' . . . On' will not coincide at all. This is because the ratio In/I0 does not follow the inverse square law and cannot be applied from one station to the other, because the applicable attenuation coefficient changes. Therefore, in the reconstructed image formed by backprojection, the points O1', O2', . . . On' will not coincide at, or cluster about, origin O; instead, they will appear to define a closed curve. Such a curve is known as an artifact; it is an image which does not accurately reflect the physical structure of the patient's body and arises because of the manner in which images are reconstructed.

Figure 4:
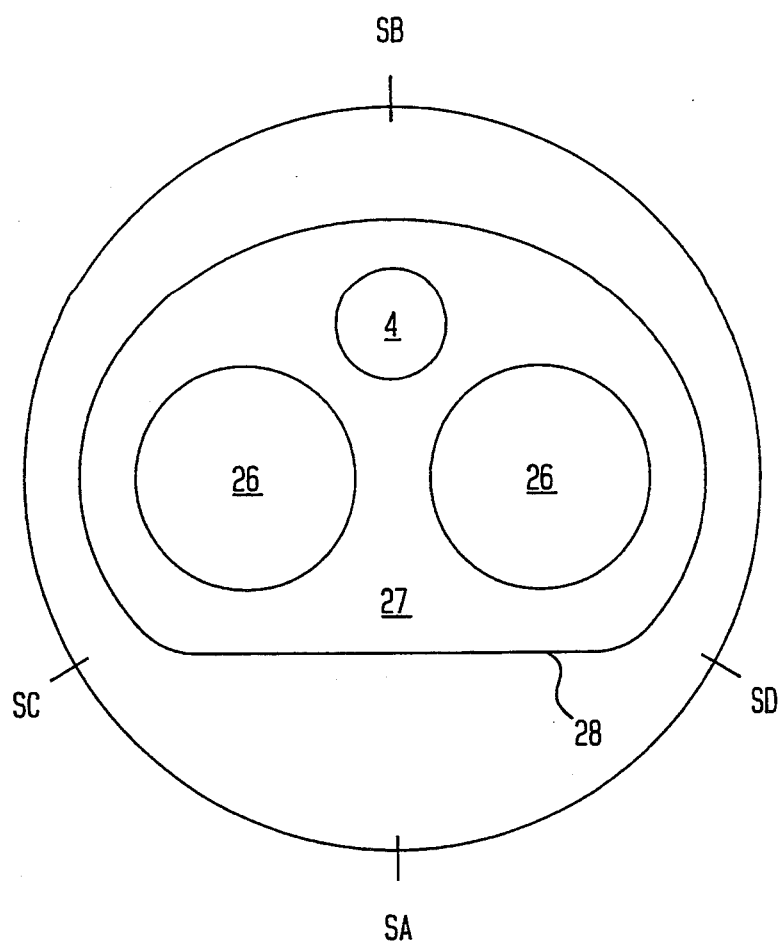
FIG. 4 schematically illustrates body structures within a slice of the patient's body.

In the case of a cardiac study, this is particularly disadvantageous. From some stations, e.g. SA and SB in FIG. 4, the heart 4 is separated from the detector 6 only by non-lung tissue 24, but from other stations, e.g. SC and SD in FIG. 4, the lungs 26 are interposed. This means that artifacts will appear in the image of the heart 4, because the attenuation coefficient of the lungs 26 differs from the attenuation coefficient of non-lung tissue 24. This problem is especially acute in triple-head cameras since these can produce excellent images, on which artifacts are especially apparent.

The invention proceeds in accordance with the realization that Compton-scattering within the slice 28 is a function of the attenuation coefficients of the various body structures (heart 4, lungs 26, non-lung tissue 24) which exist in the slice 28. This is because the scatter gradient may reasonably be expected to change at the interface between two structures (e.g. lungs 26, non-lung tissue 24) which have different attenuation coefficients.

Therefore, in accordance with the preferred embodiment of the invention, the scintillation camera system is adjusted to define an energy window which includes a range of energies associated only with Compton-scattered gamma radiation. Where the SPECT study is carried out using Tc-99m, a suitable energy window would be 90 keV–120 keV. Then, the events acquired using such a window setting are used to reconstruct a scatter image.

Figure 5:
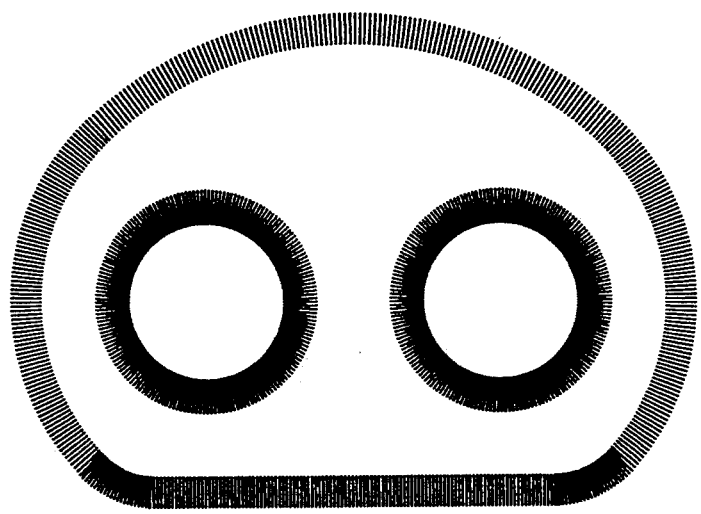
FIG. 5 shows a scatter image reconstructed in accordance with the preferred embodiment of the invention.
Figure 6:
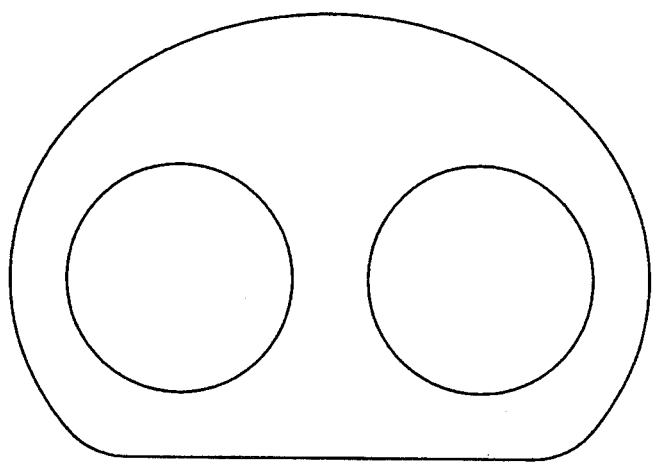
FIG. 6 shows how the FIG. 5 scatter image can be refined by image processing in accordance with the preferred embodiment of the invention.

By itself, the thus-reconstructed scatter image can (see FIG. 5) be expected to lack detail, since the mean free path of gamma ray photons at energies of interest is typically several (5–20) centimeters. Typically, the attenuation coefficient of lung tissue is about one-third that of muscle or blood or water. However, in accordance with the preferred embodiment of the invention, the scatter image is processed so as to enhance boundaries which separate regions of differing coefficients of attenuation. One method of doing this for TC-99m cardiac studies would be to compress the amplitude of scatter image pointwise, for example by taking the logarithm to form a log-scatter image. Then, differential operators, first difference operators, second difference operators or a combination of such operators could be applied to this log-scatter image. Such mathematical operations would produce edge-enhanced images which emphasize the regions where there are discontinuities in the linear attenuation coefficient, such as between lung and non-lung tissue. Ideally, such image processing would produce results such as are shown in FIG. 6.

The scatter image need not be acquired in a separate step. Modern scintillation camera systems permit more than one energy window to be defined simultaneously. Thus, it would be possible to acquire e.g. Tc-99m events using a window centered on 140 keV while acquiring scatter events falling within the referenced 90 keV–120 keV window.

In some instances, it may be sufficient to map the slice 28 into only two regions other than the heart 4: the lungs 26, and non-lung tissue 24. It may also suffice to supply for each region an attenuation coefficient which accurately represents the type of body structure involved. However, in other instances it may be advantageous to determine, empirically, what the relevant attenuation coefficients actually are. To do this, apparatus such as that which is schematically illustrated in FIG. 7 may be utilized.

Figure 7:
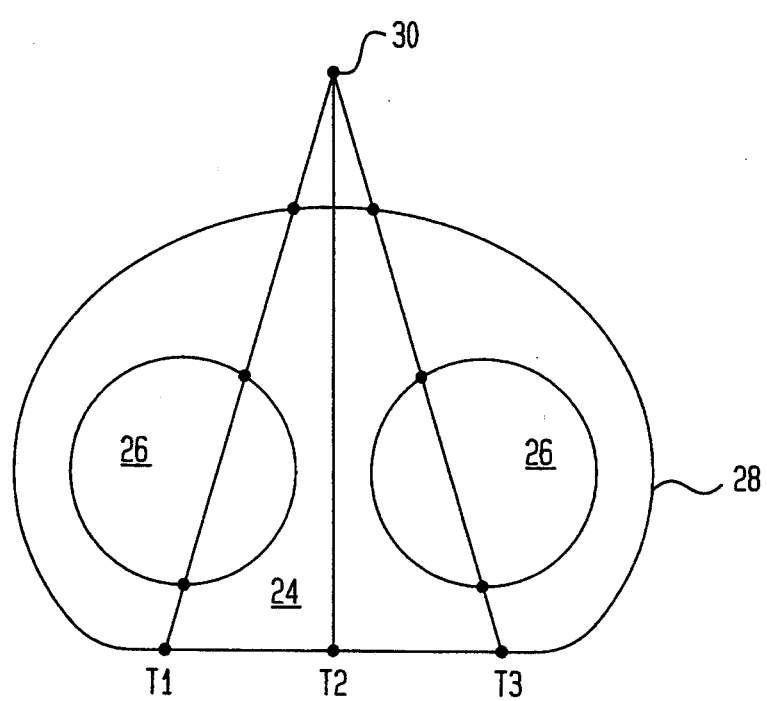
FIG. 7 shows how the attenuation coefficients of the various regions in the FIG. 6 image may be determined empirically.

FIG. 7 shows a point or line source 30 of a radioisotope which directs a plurality of rays (here, three rays) through the slice 28 where they exit with transmitted intensities T1, T2 and T3 respectively. Because the slice 28 has been mapped as shown in FIG. 6, and because the locations of the three rays are known, the radiation transmitted through the slice can be accurately approximated in accordance with the following systems of equations, wherein it is assumed that all lung tissue has the same coefficient of attenuation $\mu_2$ and that all non-lung tissue likewise has a constant coefficient of attenuation $\mu_1$:

$$T1 = e^{-\mu_1 l_{11} + \mu_2 l_{12}}$$

$$T2 = e^{-\mu_1 l_{21} + \mu_2 l_{22}}$$

$$T3 = e^{-\mu_1 l_{31} + \mu_2 l_{32}}$$

where $l_{ij}$ is the distance within a region having a linear attenuation coefficient of $\mu_j$ which is traversed by the ith ray.

Taking the logarithm of both sides yields the following system of equations:

$$S_1 = \ln T1 = -l_{11}\mu_1 + l_{12}\mu_2$$

$$S_2 = \ln T2 = -l_{21}\mu_1 + l_{22}\mu_2$$

$$S_3 = \ln T3 = -l_{31}\mu_1 + l_{32}\mu_2$$

Reformulating, $$S = L\,m$$

$$S = \begin{bmatrix} S_1 \\ S_2 \\ S_3 \end{bmatrix} \quad L = \begin{bmatrix} l_{11} & l_{12} \\ l_{21} & l_{22} \\ l_{31} & l_{32} \end{bmatrix} \quad m = \begin{bmatrix} m_1 \\ m_2 \end{bmatrix}$$

The method of least squares can be used to solve this system of equations for $\mu_1$ and $\mu_2$:

$$\mu = (L^T L)^{-1} L^T S$$

Although a preferred embodiment has been described above, the scope of the invention is limited only by the following claims.

I claim:

1. A method for using a scintillation camera system to map a slice of a patient's body into a plurality of regions in such a manner that each region may accurately be treated as having a single linear attenuation coefficient, comprising the following steps:
   conducting a SPECT study of the patient using a scintillation camera system which is set to acquire, from scintillation events caused by gamma radiation originating within said slice, those events having energies within an energy window which includes a range of energies associated only with Compton-scattered gamma radiation;
   reconstructing, from events acquired during said SPECT study, a scatter image; and
   processing said scatter image in such a manner as to define therewithin a plurality of bounded regions, each bounded region having a constant linear attenuation coefficient.

2. The method of claim 1, further comprising the steps of directing gamma rays through said slice, measuring the transmittances of said directed gamma rays, and calculating, from said measured transmittances, the attenuation coefficients of said bounded regions.

3. The method of claim 1, wherein said scintillation camera system is also set to acquire, from scintillation events caused by gamma radiation originating within said slice, those events having energies within a second energy window which includes a range of energies associated with a photopeak of a radioisotope used in said SPECT study, and further comprising the step of additionally reconstructing, from events acquired during said SPECT study which fall within said second energy window, an image of said slice.

4. The method of claim 3, further comprising the steps of directing gamma rays through said slice, measuring the transmittances of said directed gamma rays, and calculating, from said measured transmittances, the attenuation coefficients of said bounded regions, and wherein said additional reconstructing step is carried out using said calculated attenuation coefficients.

5. The method of claim 3, further comprising the steps of identifying said bounded regions by composition, assigning known attenuation coefficients to said bounded regions, and carrying out said additional reconstruction step using said known attenuation coefficients.

* * * * *